US009290737B2

(12) United States Patent
Hatta et al.

(10) Patent No.: US 9,290,737 B2
(45) Date of Patent: Mar. 22, 2016

(54) METHOD FOR ENUCLEATING NUCLEATED ERYTHROCYTE, AND ENUCLEATION INDUCER

(75) Inventors: Toshihisa Hatta, Uchinada-machi (JP); Eriko Shimamura, Uchinada-machi (JP); Hiroki Shimada, Uchinada-machi (JP)

(73) Assignee: Kanazawa Medical University, Ishikawa (JP)

( * ) Notice: Subject to any disclaimer, the term of this patent is extended or adjusted under 35 U.S.C. 154(b) by 1186 days.

(21) Appl. No.: 13/202,852

(22) PCT Filed: Feb. 23, 2010

(86) PCT No.: PCT/JP2010/001217
§ 371 (c)(1),
(2), (4) Date: Oct. 21, 2011

(87) PCT Pub. No.: WO2010/098079
PCT Pub. Date: Sep. 2, 2010

(65) Prior Publication Data
US 2012/0070897 A1 Mar. 22, 2012

(30) Foreign Application Priority Data

Feb. 24, 2009 (JP) ................................. 2009-040781

(51) Int. Cl.
*A61K 38/00* (2006.01)
*C12N 5/078* (2010.01)
*C07K 14/665* (2006.01)
*C07K 14/00* (2006.01)
*C07K 7/00* (2006.01)

(52) U.S. Cl.
CPC ............ *C12N 5/0641* (2013.01); *C07K 14/665* (2013.01); *C07K 7/00* (2013.01); *C07K 14/00* (2013.01); *C12N 2501/85* (2013.01); *C12N 2501/855* (2013.01); *C12N 2501/86* (2013.01)

(58) Field of Classification Search
None
See application file for complete search history.

(56) References Cited

U.S. PATENT DOCUMENTS 5,413,797 A * 5/1995 Khan et al. .................... 424/489
2009/0291060 A1* 11/2009 McIntosh .................... 424/85.2

FOREIGN PATENT DOCUMENTS

WO 2005/118780 A1 12/2005

OTHER PUBLICATIONS

Smith et al, Nucleotide and amino acid sequence of lymphocyte-derived corticotropin: Endotoxin induction of a truncated peptide (PNAS, vol. 87, pp. 1057-1060, 1990).*

Getting et al, MC3-R as a novel target for antiinflammatory therapy (Drug News Perspect 13(1), 2000, pp. 19-27).*
Supplementary European Search Report dated Jan. 22, 2013 issued in connection with corresponding European Application No. 10745966 (9 pages).
Uddin, Shahab et al., "Differentiation stage-specific activation of p38 mitogen-activated protein kinase isoforms in primary human erythroid cells," Proceedings of the National Academy of Sciences of the United States of America, Jan. 6, 2004, vol. 101, No. 1, pp. 147-152.
Miharada, Kenichi et al., "Efficient enucleation of erythroblasts differentiated in vitro from hematopoietic stem and progenitor cells," Nature Biotechnology, vol. 24, No. 10, Oct. 2006, pp. 1255-1256.
Hebiguchi, Miwa et al., "Dynamics of human erythroblast enucleation," International Journal of Hematology, vol. 88, No. 5, Dec. 2008, pp. 498-507.
Ray, David W. et al., "Leukemia Inhibitory Factor (LIF) Stimulates Proopiomelanocortin (POMC) Expression in a Corticotroph Cell Line. Role of STAT Pathway," Journal of Clinical Investigation, American Society for Clinical Investigation, Inc., US, vol. 97, No. 8, 1996, pp. 1852-1859.
Perone, M. J. et al., "Bilateral adrenal enucleation-induced changes in adenohypophyseal pro-opiomelanocortin (POMC)-related peptides synthesis and secretion: A comparative study with adrenalectomized rats," Journal of Endocrinological Investigation, vol. 20, No. 4, 1997, pp. 172-182.
International Search Report dated Apr. 20, 2010 issued in connection with corresponding International Application No. PCT/JP2010/001217 (2 pages).
Soni, S. et al., "Absence of Erythroblast Macrophage Protein (Emp) Leads to Failure of Erythroblast Nuclear Extrusion," Journal of Biological Chemistry, Jul. 21, 2006, vol. 281(29), pp. 20181-20189.
Sonoda, Y. et al., "Effects of Colchicine on the Enucleation of Erythroid Cells and Macrophages in the Liver of Mouse Embryos: Ultrastructural and Three-Dimensional Studies," The Anatomical Record, 1998, vol. 251(3), pp. 290-296.
Peng, J. et al., "Enucleation of cultured mouse fetal erythroblasts requires Rac GTPases and mDia2," Nature Cell Biology, Mar. 2008, vol. 10(3), pp. 314-321.
Ma, F. et al., "Generation of functional erythrocytes from human embryonic stem cell-derived definitive hematopoiesis," Proceedings of the National Acadamy of Sciences U.S.A., Sep. 2, 2008, vol. 105, No. 35, pp. 13087-13092.

(Continued)

*Primary Examiner* — Karlheinz R Skowronek
*Assistant Examiner* — Sergio Coffa
(74) *Attorney, Agent, or Firm* — Kilyk & Bowersox, P.L.L.C.

(57) ABSTRACT

Provided is a factor capable of inducing enucleation, which is a final stage of erythrocyte differentiation, within a short time. More particularly, provided are a method of inducing enucleation, which is a final stage of erythrocyte differentiation, within a short time by adding a compound derived from proopiomelanocortin (POMC) to an undifferentiated (nucleated) erythrocyte, and an enucleation inducer including the compound.

3 Claims, 7 Drawing Sheets

(56) References Cited

OTHER PUBLICATIONS

Murao, K. et al., "Expression of Truncated Pro-Opiomelanocortin Gene Transcript in Human Leukemia Cell Lines," Endrocine Journal, 1998, vol. 45(3), pp. 399-405.

EPO Communication pursuant to Article 94(3) EPC dated Dec. 19, 2013 in corresponding European Patent Application No. 10 745 966.1 (5 pages).
EPO Communication pursuant to Article 94(3) EPC dated Dec. 10, 2014 in corresponding European Patent Application No. 10 745 966.1 (4 pages).

* cited by examiner

NUMERALS INDICATE A RANGE OF TOTAL AMINO ACIDS WHEN THE FIRST AMINO ACID OF ACTH (TOTAL AMINO ACID RESIDUE: 39) WAS DESIGNATED AS 1.

(a) NUCLEATED CELLs
(b) CELL WHICH IS BEING ENUCLEATED (NUCLEATED CELL)
(c) ERYTHROCYTE WHICH HAS BEEN ENUCLEATED

METHOD FOR ENUCLEATING NUCLEATED ERYTHROCYTE, AND ENUCLEATION INDUCER

TECHNICAL FIELD

The present application is a National Stage Application of PCT/JP2010/001217, filed Feb. 23, 2010, which claims priority from Japanese Patent Application Laid-open No. 2009-040781, filed Feb. 24, 2009, which are incorporated herein by reference.

The present invention relates to a method of inducing enucleation, which is a final stage of erythrocyte differentiation, within a short time by adding a compound derived from proopiomelanocortin (POMC) to an undifferentiated (nucleated) erythrocyte, and an enucleation inducer including the compound.

BACKGROUND ART

Currently, blood transfusion is mainly supported by blood donation in the medical field, but numerous efforts and costs are required for its collection, examination of infections and the like, and storage in order to assure its supply. In order to supply sufficient amounts of blood in the medical and research fields, a method of inducing a mature erythrocyte from a cultured hematopoietic stem cell within a short time and efficiently is required. If a technology for culturing a hematopoietic stem cell from a totipotent or pluripotent stem cell including an iPS cell, an ES cell, and the like is developed and practically applied in future, the cell can be artificially cultured in all of the steps and stable supply of blood with a low risk of infection becomes possible, which highly contributes to medical procedures. Further, industrial culture of blood in a large amount becomes possible, and thus blood production with a low cost and its development as a medical industry can be expected.

An erythrocyte is an important blood component which carries oxygen, but the erythrocyte itself cannot proliferate because it has no nucleus. Thus, in vivo, an erythroid precursor cell, which is a cell at a stage prior to the erythrocyte, proliferates and matures through "enucleation" which is deprived of the nucleus.

Therefore, in order to produce the erythrocyte in a large amount, mass culture of the erythroid precursor cell is needed, and thus, establishment of a "cell line (erythroid precursor cell line)" is needed.

Further, in the research for hematopoiesis, the group of Ihle et al. reported that "SOCS3 was essential for hematopoiesis in the fetal liver" (see Non Patent Literature 1).

In addition, the group of Nagata et al. reported that "fetal DNase II knockout mice were not able to produce a mature erythrocyte and experienced severe anemia, and macrophage DNase II in the fetal liver was important as a support for the erythrocyte differentiation" (see Non Patent Literature 2).

Meanwhile, the group of RIKEN established an erythroid precursor cell line from a murine ES cell and enabled the culture of an erythroid precursor cell in a large amount in vitro (see Non Patent Literature 3).

As the mass culture is available, a method of directly transfusing an erythroid precursor cell into a body is also possible. However, safety aspects such as canceration are largely concerned because the precursor cell is nucleated. In actuality, it is necessary to develop an induction method including further differentiating the precursor cell for enucleation to obtain a mature erythrocyte with no nucleus.

Further, the method of producing a mature erythrocyte utilizing cord blood reported by Miharada et al. (Non Patent Literature 4) discloses that "the generation of a mature enucleated erythrocyte from an erythroid precursor cell required culture for 20 days and the ratio of a final enucleated cell was 77%."

In the method of producing a mature erythrocyte, no factor for inducing enucleation is added to a medium, the erythroid precursor cell is differentiated by a differentiation-inducing factor added in an early phase of the culture, and the enucleation is induced as natural maturation associated therewith.

As described above, several methods of producing an erythroid precursor cell have already been known, but a technology for enucleating a nucleated erythrocyte within a short time and with high efficiency during the process has been little known. However, there is the following report on a method of adding no factor for inducing enucleation to a medium (see Patent Literature 1).

Patent Literature 1 discloses a "method of inducing enucleation by culturing a hematopoietic stem cell in the absence of erythropoietin." However, an enucleation rate is 1 to 5% on Day 11 and 65 to 80% on Day 15. That is, the induction of enucleation takes a long time and the enucleation rate is also insufficient.

From the above-mentioned background, a nucleated erythrocyte remains at a ratio of about 20 to 30% in an erythrocyte preparation obtained by a currently available production method, and further the administration of such erythrocyte in vivo has a risk of canceration, which is problematic.

In addition, in future, the induction of a nucleated erythrocyte in a large amount from a human iPS or ES cell becomes possible, and as a result, it is expected that a method of inducing enucleation of an erythrocyte within a short time is demanded.

CITATION LIST

Patent Literature

[PTL 1] WO 2005/118780 A1

Non Patent Literature

[NPL 1] Jean-Christophe et al., Cell. 1999; 98(5): 617-27.
[NPL 2] Kawane K. et al., Science. 2001; 292(5521): 1546-9.
[NPL 3] Hiroyama T. et al., PLoS ONE. 2008; 3 (2): e1544.
[NPL 4] Miharada K. et al., Nat. Biotechnol. 2006; 24(10): 1255-6.

SUMMARY OF INVENTION

Technical Problem

From the above-mentioned background, it is an object of the present invention to provide a novel method of inducing enucleation actively and within a short time, and a novel enucleation inducer.

More particularly, it is an object of the present invention to provide a factor capable of inducing enucleation, which is a final stage of erythrocyte differentiation, within a short time.

Solution to Problem

In order to solve the above-mentioned problem, the present invention has the following features.

"1. A method of enucleating a nucleated erythrocyte, including culturing a separated nucleated erythrocyte in a culture medium containing a compound derived from proopiomelanocortin (POMC).

2. A method of enucleating a nucleated erythrocyte according to the item 1, in which the compound is selected from any one of the following compounds:
(1) Proopiomelanocortin (POMC);
(2) Adrenocorticotropic Hormone (ACTH);
(3) Melanocyte Stimulating Hormone (MSH);
(4) Lipotrophin (LPH);
(5) endorphin;
(6) Corticotropin-Like Intermediate Lobe Peptide (CLIP); and
(7) a protected derivative, a glycosylated product, an acylated derivative, or an acetylated derivative of the compound according to any one of the above-mentioned items (1) to (6).

3. A method of enucleating a nucleated erythrocyte according to the item 1, in which the compound is selected from any one of the following compounds:
(1) ACTH;
(2) α-MSH;
(3) CLIP; and
(4) a protected derivative, a glycosylated product, an acylated derivative, or an acetylated derivative of the compound according to any one of the above-mentioned items (1) to (3).

4. A method of enucleating a nucleated erythrocyte according to claim 1, in which the compound is selected from any one of the following peptides:
(1) a peptide set forth in SEQ ID NO: 1;
(2) a peptide set forth in SEQ ID NO: 2;
(3) a peptide set forth in SEQ ID NO: 3;
(4) a peptide set forth in SEQ ID NO: 4;
(5) a peptide set forth in SEQ ID NO: 5;
(6) a peptide set forth in SEQ ID NO: 6;
(7) a peptide set forth in SEQ ID NO: 7;
(8) a peptide set forth in SEQ ID NO: 8;
(9) a peptide set forth in SEQ ID NO: 9;
(10) a peptide set forth in SEQ ID NO: 10;
(11) a peptide set forth in SEQ ID NO: 11;
(12) a peptide set forth in SEQ ID NO: 12;
(13) a peptide set forth in SEQ ID NO: 13;
(14) a peptide set forth in SEQ ID NO: 14;
(15) a peptide set forth in SEQ ID NO: 15;
(16) a peptide set forth in SEQ ID NO: 16;
(17) a peptide set forth in SEQ ID NO: 17;
(18) a peptide set forth in SEQ ID NO: 18;
(19) a peptide set forth in SEQ ID NO: 19;
(20) a peptide including the peptide according to any one of the above-mentioned items (1) to (19);
(21) a protected derivative, a glycosylated product, an acylated derivative, or an acetylated derivative of the peptide according to any one of the above-mentioned items (1) to (19);
(22) a peptide having 90% or more homology to the peptide according to any one of the above-mentioned items (1) to (19) and having substantially the same enucleation induction action on a nucleated erythrocyte as the peptide; and
(23) a peptide having 1 to 5 amino acid substitutions, deletions, insertions, and/or additions in the peptide according to any one of the above-mentioned items (1) to (19) and having substantially the same enucleation induction action on a nucleated erythrocyte as the peptide.

5. A method of enucleating a nucleated erythrocyte according to the item 1, in which the compound is selected from any one of the following peptides:
(1) a peptide set forth in SEQ ID NO: 1;
(2) a peptide set forth in SEQ ID NO: 2;
(3) a peptide set forth in SEQ ID NO: 3;
(4) a peptide set forth in SEQ ID NO: 11;
(5) a peptide set forth in SEQ ID NO: 12;
(6) a peptide including the peptide according to any one of the above-mentioned items (1) to (5);
(7) a protected derivative, a glycosylated product, an acylated derivative, or an acetylated derivative of the peptide according to any one of the above-mentioned items (1) to (5);
(8) a peptide having 90% or more homology to the peptide according to any one of the above-mentioned items (1) to (5) and having substantially the same enucleation induction action on a nucleated erythrocyte as the peptide; and
(9) a peptide having 1 to 5 amino acid substitutions, deletions, insertions, and/or additions in the peptide according to any one of the above-mentioned items (1) to (5) and having substantially the same enucleation induction action on a nucleated erythrocyte as the peptide.

6. A method of enucleating a nucleated erythrocyte according to any one of the items 1 to 5, in which the concentration of the compound in a culture medium is 0.01 to 20.0 μM.

7. A enucleated erythrocyte, which is obtained by the method of enucleating a nucleated erythrocyte according to any one of the items 1 to 6.

8. An enucleation inducer, including a compound derived from POMC.

9. An enucleation inducer according to the item 8, in which the compound is selected from any one of the following compounds:
(1) POMC;
(2) ACTH;
(3) MSH;
(4) LPH;
(5) endorphin;
(6) CLIP; and
(7) a protected derivative, a glycosylated product, an acylated derivative, or an acetylated derivative of the compound according to any one of the above-mentioned items (1) to (6).

10. An enucleation inducer according to the item 8, in which the compound is selected from any one of the following compounds:
(1) ACTH;
(2) α-MSH;
(3) CLIP; and
(4) a protected derivative, a glycosylated product, an acylated derivative, or an acetylated derivative of one according to any one of the above-mentioned items (1) to (3).

11. An enucleation inducer according to the item 8, in which the compound is selected from any one of the following peptides:
(1) a peptide set forth in SEQ ID NO: 1;
(2) a peptide set forth in SEQ ID NO: 2;
(3) a peptide set forth in SEQ ID NO: 3;
(4) a peptide set forth in SEQ ID NO: 4;
(5) a peptide set forth in SEQ ID NO: 5;
(6) a peptide set forth in SEQ ID NO: 6;
(7) a peptide set forth in SEQ ID NO: 7;
(8) a peptide set forth in SEQ ID NO: 8;
(9) a peptide set forth in SEQ ID NO: 9;
(10) a peptide set forth in SEQ ID NO: 10;
(11) a peptide set forth in SEQ ID NO: 11;
(12) a peptide set forth in SEQ ID NO: 12;
(13) a peptide set forth in SEQ ID NO: 13;

(14) a peptide set forth in SEQ ID NO: 14;
(15) a peptide set forth in SEQ ID NO: 15;
(16) a peptide set forth in SEQ ID NO: 16;
(17) a peptide set forth in SEQ ID NO: 17;
(18) a peptide set forth in SEQ ID NO: 18;
(19) a peptide set forth in SEQ ID NO: 19;
(20) a peptide including the peptide according to any one of the above-mentioned items (1) to (19);
(21) a protected derivative, a glycosylated product, an acylated derivative, or an acetylated derivative of the peptide according to any one of the above-mentioned items (1) to (19);
(22) a peptide having 90% or more homology to the peptide according to any one of the above-mentioned items (1) to (19) and having substantially the same enucleation induction action upon a nucleated erythrocyte as the peptide; and
(23) a peptide having 1 to 5 amino acid substitutions, deletions, insertions, and/or additions in the peptide according to any one of the above-mentioned items (1) to (19) and having substantially the same enucleation induction action on a nucleated erythrocyte as the peptide.

12. An enucleation inducer according to the item 8, in which the compound is selected from any one of the following peptides:
(1) a peptide set forth in SEQ ID NO: 1;
(2) a peptide set forth in SEQ ID NO: 2;
(3) a peptide set forth in SEQ ID NO: 3;
(4) a peptide set forth in SEQ ID NO: 11;
(5) a peptide set forth in SEQ ID NO: 12;
(6) a peptide including the peptide according to any one of the above-mentioned items (1) to (5);
(7) a protected derivative, a glycosylated product, an acylated derivative, or an acetylated derivative of the peptide according to any one of the above-mentioned items (1) to (5);
(8) a peptide having 90% or more homology to the peptide according to any one of the above-mentioned items (1) to (5) and having substantially the same enucleation induction action on a nucleated erythrocyte as the peptide; and
(9) a peptide having 1 to 5 amino acid substitutions, deletions, insertions, and/or additions in the peptide according to any one of the above-mentioned items (1) to (5) and having substantially the same enucleation induction action on a nucleated erythrocyte as the peptide.

13. A method of culturing and/or proliferating an enucleated erythrocyte, including culturing a hematopoietic stem cell or an erythroid precursor cell in a culture medium containing a compound derived from POMC.

14. A method of culturing and/or proliferating an enucleated erythrocyte according to the item 13, in which the culture medium contains a cytokine.

15. A method of culturing and/or proliferating an enucleated erythrocyte according to the item 13 or 14, in which the compound is selected from any one of the following compounds:
(1) POMC;
(2) ACTH;
(3) MSH;
(4) LPH;
(5) endorphin;
(6) CLIP; and
(7) a protected derivative, a glycosylated product, an acylated derivative, or an acetylated derivative of the compound according to any one of the above-mentioned items (1) to (6).

16. A method of culturing and/or proliferating an enucleated erythrocyte according to the item 13 or 14, in which the compound is selected from any one of the following compounds:
(1) ACTH;
(2) α-MSH;
(3) CLIP; and
(4) a protected derivative, a glycosylated product, an acylated derivative, or an acetylated derivative of the compound according to any one of the above-mentioned items (1) to (3).

17. A method of culturing and/or proliferating an enucleated erythrocyte according to the item 13 or 14, in which the compound is selected from any one of the following peptides:
(1) a peptide set forth in SEQ ID NO: 1;
(2) a peptide set forth in SEQ ID NO: 2;
(3) a peptide set forth in SEQ ID NO: 3;
(4) a peptide set forth in SEQ ID NO: 4;
(5) a peptide set forth in SEQ ID NO: 5;
(6) a peptide set forth in SEQ ID NO: 6;
(7) a peptide set forth in SEQ ID NO: 7;
(8) a peptide set forth in SEQ ID NO: 8;
(9) a peptide set forth in SEQ ID NO: 9;
(10) a peptide set forth in SEQ ID NO: 10;
(11) a peptide set forth in SEQ ID NO: 11;
(12) a peptide set forth in SEQ ID NO: 12;
(13) a peptide set forth in SEQ ID NO: 13;
(14) a peptide set forth in SEQ ID NO: 14;
(15) a peptide set forth in SEQ ID NO: 15;
(16) a peptide set forth in SEQ ID NO: 16;
(17) a peptide set forth in SEQ ID NO: 17;
(18) a peptide set forth in SEQ ID NO: 18;
(19) a peptide set forth in SEQ ID NO: 19;
(20) a peptide including the peptide according to any one of the above-mentioned items (1) to (19);
(21) a protected derivative, a glycosylated product, an acylated derivative, or an acetylated derivative of the peptide according to any one of the above-mentioned items (1) to (19);
(22) a peptide having 90% or more homology to the peptide according to any one of the above-mentioned items (1) to (19) and having substantially the same enucleation induction action on a nucleated erythrocyte as the peptide; and
(23) a peptide having 1 to 5 amino acid substitutions, deletions, insertions, and/or additions in the peptide according to any one of the above-mentioned items (1) to (19) and having substantially the same enucleation induction action on a nucleated erythrocyte as the peptide.

18. A method of culturing and/or proliferating an enucleated erythrocyte according to the item 13 or 14, in which the compound is selected from any one of the following peptides:
(1) a peptide set forth in SEQ ID NO: 1;
(2) a peptide set forth in SEQ ID NO: 2;
(3) a peptide set forth in SEQ ID NO: 3;
(4) a peptide set forth in SEQ ID NO: 11;
(5) a peptide set forth in SEQ ID NO: 12;
(6) a peptide including the peptide according to any one of the above-mentioned items (1) to (5);
(7) a protected derivative, a glycosylated product, an acylated derivative, or an acetylated derivative of the peptide according to any one of the above-mentioned items (1) to (5);
(8) a peptide having 90% or more homology to the peptide according to any one of the above-mentioned items (1) to (5) and having substantially the same enucleation induction action on a nucleated erythrocyte as the peptide; and
(9) a peptide having 1 to 5 amino acid substitutions, deletions, insertions, and/or additions in the peptide according to any one of the above-mentioned items (1) to (5) and having substantially the same enucleation induction action on a nucleated erythrocyte as the peptide.

19. An enucleated erythrocyte, which is obtained by the method of culturing and/or proliferating an enucleated erythrocyte according to any one of the items 13 to 18.

20. An enucleation inducer, in which the enucleation inducer induces enucleation in vitro through an action on MC1R, MC2R, MC3R, MC4R, and/or MC5R, which is a melanocortin receptor expressed on a nucleated erythrocyte.

21. A method of enucleating a nucleated erythrocyte, including inducing enucleation in vitro through an action on MC1R, MC2R, MC3R, MC4R, and/or MC5R, which is a melanocortin receptor expressed on a nucleated erythrocyte.

Advantageous Effects of Invention

The present invention can provide the method of inducing enucleation, which is a final stage of erythrocyte differentiation, within a short time by adding a compound derived from POMC to an undifferentiated (nucleated) erythrocyte, and the enucleation inducer including the compound.

This enables shortening of a period of producing blood and removal of a risk of canceration associated with transfusion of nucleated erythrocytes. That is, safe blood can be obtained within a short time and stably, and this greatly contributes to medical technologies.

DESCRIPTION OF EMBODIMENTS

Figure 1:
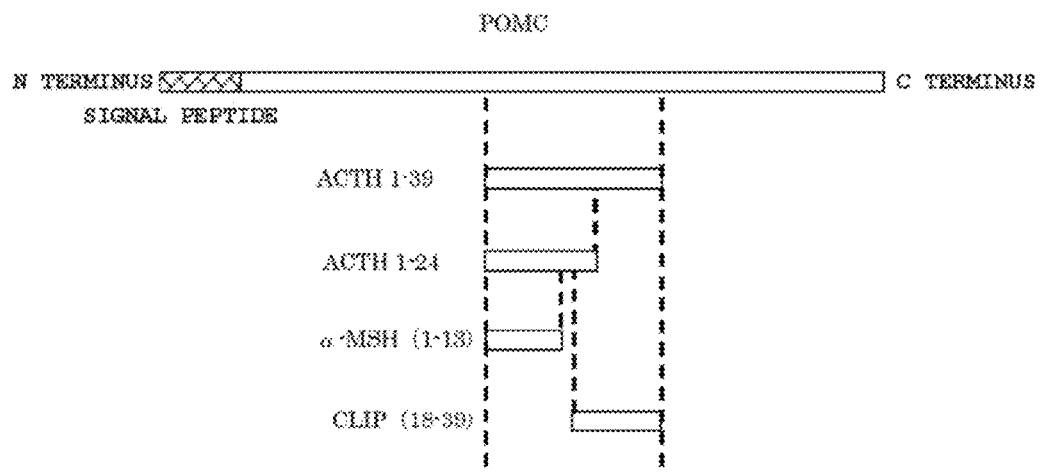
FIG. 1 shows a structure of POMC.

The present invention has the features as described above, and embodiments thereof are described below.

(Hematopoietic Stem Cell)

A "hematopoietic stem cell" of the present invention is a cell having an ability to differentiate into any kinds of blood cells as well as having a hematopoietic repopulating ability. These cells are mainly present in bone marrow, cord blood, spleen and liver, and also present in peripheral blood although being a rare population. A "stem cell" means a pluripotent hematopoietic stem cell or a myeloid stem cell differentiated therefrom (CFU-GEMM). These cells are CD34-positive and CD133-positive cells.

The hematopoietic stem cell can be obtained by methods known per se. For example, the hematopoietic stem cell can be obtained by separating the hematopoietic stem cell present in the bone marrow, the cord blood, the spleen, the liver or the peripheral blood described above using a cell sorter (flow cytometry or the like).

More particularly, the hematopoietic stem cell can be isolated using a commercially available antibody capable of binding to a hematopoietic stem cell surface antigen (e.g., CD34) and using a method well-known to those skilled in the art. For example, the antibody is bound to magnetic beads, and an immunological method is used for recovering a desired cell type. Preferably, the hematopoietic stem cell is in the form of a CD34-positive cell. In fact, CD34 is known as a standard marker for the hematopoietic stem cell.

The CD34-positive cells can be separated by many various methods. Most widely utilized is a positive immunological selection based on binding the cell to an anti-CD34 antibody (Cellpro, Baxter, Myltenyi) immobilized on a solid support. Other selection methods include a negative selection for isolating all cells which do not express CD34 from the CD34-positive cells based on the expression of a cell lineage-specific cell surface antigen. In addition, the hematopoietic stem cells to be cultured can also be produced from embryonic stem cells ex vivo (see WO 01/34776 A1, U.S. Pat. No. 6,613,568 B).

Alternatively, for example, human cord blood CD34-positive cells (available from RIKEN, Cell Bank) can be utilized.

(Erythroid Precursor Cell)

An "erythroid precursor cell" of the present invention means a cell which can differentiate into a blood cell in only one direction to an erythroid cell lineage although its differentiated stage can not be identified morphologically from the hematopoietic stem cell.

Specifically, a platelet colony forming cell (CFU-MEG), an eosinophil colony forming cell (CFU-EO), a granulocyte-monocyte colony forming cell (CFU-GM), an erythrocyte forming cell (BFU-E, CFU-E), a T precursor cell, a B precursor cell, and the like are included. All of them are CD34-positive cells.

The erythroid precursor cell can be obtained by methods known per se. For example, the erythroid precursor cell can be obtained by separating the erythroid precursor cell present in the bone marrow, the cord blood, the spleen, the liver or the peripheral blood described above using a cell sorter (flow cytometry or the like).

In addition, a method including inducing the erythroid precursor cell from a murine ES cell is also known (see Non Patent Literature 3).

In addition, attempts have been made to develop various methods and optimal culture conditions in order to grow the hematopoietic stem cell or the erythroid precursor cell in a large amount. Further, several reports are available as follows.

Thus, the hematopoietic stem cell or the erythroid precursor cell to be used in the present invention can also be obtained by utilizing the method described below.

(1) Method including proliferating a hematopoietic stem cell by co-culturing the hematopoietic stem cell with a stromal cell derived from a mammalian animal (see JP 10-295369 A).

(2) Method including obtaining a hematopoietic stem cell by proliferating cells obtained from the human cord blood and having a hematopoiesis supporting ability, in vitro (see JP 2002-6520 A).

(3) Method including culturing a human hematopoietic stem cell or erythroid precursor cell in coexistence of stromal cells derived from human placental tissue or cord tissue (see JP 2004-222502 A).

(4) Method including culturing and proliferating a hematopoietic stem cell or an erythroid precursor cell using an endometrial cell (see JP 2007-525231 A).

(Nucleated Erythrocyte)

A "nucleated erythrocyte" of the present invention is used for distinguishing from an enucleated erythrocyte (mature erythrocyte).

A wide variety of methods of preparing the nucleated erythrocyte has been reported, and a method known per se can be utilized. For example, the "method including adding a water-soluble polymer compound to collected whole blood to aggregate and precipitate an erythrocyte selectively and progressively" described in WO 2004/012750 A1 can be utilized, but the method is not particularly limited.

In addition, a method including differentiating a hematopoietic stem cell or an erythroid precursor cell derived from the cord blood into a nucleated erythrocyte is also known (see Non Patent Literature 4).

An origin of each of the hematopoietic stem cell, the erythroid precursor cell, and the nucleated erythrocyte described above is not particularly limited as long as they are derived from a mammal. Preferably, the mammal is exemplified by a human, a dog, a cat, a mouse, a rat, a rabbit, a swine, a horse, and the like, but the mammal is more preferably a human. The hematopoietic stem cell, the erythroid precursor cell, and the nucleated erythrocyte described above that are derived from the human refer to those separated from a living body.

(Compound Derived from POMC)

The "compound derived from POMC" of the present invention refers to POMC, MSH (α-, β-, γ-MSH), ACTH, LPH (γ-, β-LPH), endorphin (α, β, γ-endorphin), or CLIP, or protected derivatives thereof, glycosylated ones, acylated derivatives, or acetylated derivatives thereof.

The protected derivatives thereof, the glycosylated ones, the acylated derivatives, or the acetylated derivatives thereof can be obtained by methods known per se.

POMC is a glycoprotein with a molecular weight of about 31,100 produced in pituitary (pro-hormone), and a precursor of a series of corticotropic hormones which bring many effects to a host.

POMC is the precursor of melanocyte stimulating hormone (MSH), adrenocorticotropin (ACTH), lipotrophin (LPH), Corticotropin-Like Intermediate Lobe Peptide (CLIP), and β-endorphin. All of these hormones are produced by being cut out from only one large precursor, POMC (see FIG. 1).

The adrenocorticotropic hormone {(ACTH), adrenocorticotropin: adrenal cortex stimulating hormone} is produced and secreted in an anterior pituitary ACTH producing cell by an action of a corticotropin releasing factor (CRF), which is a hypothalamus hormone. ACTH is a peptide formed of the following amino acid residues. In addition herein, ACTH is sometimes referred to as ACTH1-39 in order to discriminate ACTH from the following ACTH fragment sequences.

(SEQ ID NO: 1)
Ser-Tyr-Ser-Met-Glu-His-Phe-Arg-Trp-Gly-Lys-Pro-

Val-Gly-Lys-Lys-Arg-Arg-Pro-Val-Lys-Val-Tyr-Pro-

Asn-Val-Ala-Glu-Asn-Glu-Ser-Ala-Glu-Ala-Phe-Pro-

Leu-Glu-Phe

In addition, various ACTH fragment sequences are known. Those fragment sequences themselves are each considered to have an enucleation action.

ACTH1-24 (sequence at positions 1 to 24 of ACTH) is a peptide formed of the following amino acid residues.

(SEQ ID NO: 2)
Ser-Tyr-Ser-Met-Glu-His-Phe-Arg-Trp-Gly-Lys-Pro-

Val-Gly-Lys-Lys-Arg-Arg-Pro-Val-Lys-Val-Tyr-Pro

ACTH1-10 (sequence at positions 1 to 10 of ACTH) is a peptide formed of the following amino acid residues.

(SEQ ID NO: 13)
Ser-Tyr-Ser-Met-Glu-His-Phe-Arg-Trp-Gly

ACTH1-14 (sequence at positions 1 to 14 of ACTH) is a peptide formed of the following amino acid residues.

(SEQ ID NO: 14)
Ser-Tyr-Ser-Met-Glu-His-Phe-Arg-Trp-Gly-Lys-Pro-

Val-Gly

ACTH1-16 (sequence at positions 1 to 16 of ACTH) is a peptide formed of the following amino acid residues.

(SEQ ID NO: 15)
Ser-Tyr-Ser-Met-Glu-His-Phe-Arg-Trp-Gly-Lys-Pro-

Val-Gly-Lys-Lys

ACTH1-17 (sequence at positions 1 to 17 of ACTH) is a peptide formed of the following amino acid residues.

(SEQ ID NO: 16)
Ser-Tyr-Ser-Met-Glu-His-Phe-Arg-Trp-Gly-Lys-Pro-

Val-Gly-Lys-Lys-Arg

ACTH4-10 (sequence at positions 4 to 10 of ACTH) is a peptide formed of the following amino acid residues.

(SEQ ID NO: 17)
Met-Glu-His-Phe-Arg-Trp-Gly

ACTH7-38 (sequence at positions 7 to 38 of ACTH) is a peptide formed of the following amino acid residues.

(SEQ ID NO: 18)
Phe-Arg-Trp-Gly-Lys-Pro-Val-Gly-Lys-Lys-Arg-Arg-

Pro-Val-Lys-Val-Tyr-Pro-Asn-Val-Ala-Glu-Asn-Glu-

Ser-Ala-Glu-Ala-Phe-Pro-Leu-Glu

ACTH4-9 (sequence at positions 4 to 9 of ACTH) is a peptide formed of the following amino acid residues.

(SEQ ID NO: 19)
Met-Glu-His-Phe-Arg-Trp

The melanocyte-stimulating hormone (MSH) is a peptide hormone produced in the intermediate pituitary gland, and α-MSH, β-MSH, and γ-MSH are known to exist.

α-MSH is a peptide being formed of the following amino acid residues and containing an acetyl group.

(SEQ ID NO: 3)
Acetyl-(N)-Ser-Tyr-Ser-Met-Glu-His-Phe-Arg-Trp-

Gly-Lys-Pro-Val-NH₂

β-MSH is a peptide formed of the following amino acid residues.

(SEQ ID NO: 4)
Ala-Glu-Lys-Lys-Asp-Glu-Gly-Pro-Tyr-Arg-Met-Glu-

His-Phe-Arg-Trp-Gly-Ser-Pro-Pro-Lys-Asp

γ-MSH is a peptide formed of the following amino acid residues.

(SEQ ID NO: 5)
Tyr-Val-Met-Gly-His-Phe-Arg-Trp-Asp-Arg-Phe-Gly

The lipotropic hormone {(lipotropin), LPH} is a single-chain polypeptide produced in the anterior and intermediate pituitary glands, and γ-LPH and β-LPH are known.

γ-LPH is a peptide formed of the following amino acid residues.

(SEQ ID NO: 6)
Tyr-Gly-Gly-Phe-Met-Thr-Ser-Glu-Lys-Ser-Gln-Thr-

Pro-Leu-Val-Thr-Leu

β-LPH is a peptide formed of the following amino acid residues.

(SEQ ID NO: 7)
Tyr-Gly-Gly-Phe-Met-Thr-Ser-Glu-Lys-Ser-Gln-Thr-

Pro-Leu-Val-Thr-Tyr-Gly-Gly-Phe-Met-Thr-Ser-Glu-

Lys-Ser-Gln-Thr-Pro-Leu-Val-Thr

The endorphin is an endogenous opioid peptide that exists in the brain and pituitary gland of a mammal, and three kinds of endorphins, i.e., α-endorphin, β-endorphin, and γ-endorphin are known.

α-Endorphin is a peptide formed of the following amino acid residues.

(SEQ ID NO: 8)
Tyr-Gly-Gly-Phe-Met-Thr-Ser-Glu-Lys-Ser-Gln-Thr-

Pro-Leu-Val-Thr-Tyr-Gly-Gly-Phe-Met-Thr-Ser-Glu-

Lys-Ser-Gln-Thr-Pro-Leu-Val-Thr

β-Endorphin is a peptide formed of the following amino acid residues.

(SEQ ID NO: 9)
Tyr-Gly-Gly-Phe-Met-Thr-Ser-Glu-Lys-Ser-Gln-Thr-

Pro-Leu-Val-Thr-Leu-Phe-Lys-Asn-Ala-Ile-Ile-Lys-

Asn-Ala-Tyr-Lys-Lys-Gly-Glu

γ-Endorphin is a peptide formed of the following amino acid residues.

(SEQ ID NO: 10)
Tyr-Gly-Gly-Phe-Met-Thr-Ser-Glu-Lys-Ser-Gln-Thr-

Pro-Leu-Val-Thr-Leu

The Corticotropin-Like Intermediate Lobe Peptide (CLIP) is a peptide formed of the following amino acid residues.

(SEQ ID NO: 11)
Arg-Pro-Val-Lys-Val-Tyr-Pro-Asn-Gly-Ala-Glu-Asp-

Glu-Ser-Ala-Glu-Ala-Phe-Pro-Leu-Glu-Phe

In MSH (α-, β-, γ-MSH), ACTH, LPH (γ-, β-LPH), endorphin (α, β, γ-endorphin), or CLIP described above, their amino acid sequence is sometimes partially different among species.

For example, concerning ACTH, whales have the same sequence as SEQ ID NO: 1, but Ser at position 31 is substituted with Leu in SEQ ID NO: 1 in swines, and Glu at position 33 is substituted with Gln in SEQ ID NO: 1 in sheep and cattle.

In the present invention, MSH (α-, β-, γ-MSH), ACTH, LPH (γ-, β-LPH), endorphin (α, β, γ-endorphin), and CLIP having different sequences among species are each also included as the compound derived from POMC.

Further, the results of Examples 1 to 5 below have confirmed that ACTH1-39, ACTH1-24, and CLIP each have an enucleation induction action on an erythrocyte. Thus, it is conceivable that a peptide having the following amino acid residues which are common to ACTH1-39, ACTH1-24, and CLIP plays a role for the enucleation induction action on an erythrocyte. Thus, the following peptide is also included as the compound derived from POMC.

(SEQ ID NO: 12)
Arg-Pro-Val-Lys-Val-Try-Pro

Further, the present invention also includes a peptide containing any of the peptides described above, a peptide having 90% or more homology to any of the peptides described above and having substantially the same enucleation induction action on an erythrocyte as the peptide, and a peptide having 1 to 5 amino acid substitutions, deletions, insertions and/or additions in any of the peptides described above and having substantially the same enucleation induction action on an erythrocyte as the peptide, as the compound derived from POMC.

The "peptide containing the peptide set forth in SEQ ID NO: 1" means a peptide keeping substantially the same enucleation action on an erythrocyte as the peptide set forth in SEQ ID NO: 1 and having any 1 to 30, 1 to 20, 1 to 10, or 1 to 5 amino acid additions to the N terminus and/or the C terminus.

"Substantially the same enucleation induction action as the peptide set forth in SEQ ID NO: 1" means having the enucleation action of the peptide on a nucleated erythrocyte, and its degree may be stronger or weaker than the enucleation action of the peptide.

It is appropriate for the "sequence homology" to be typically 70% or more, preferably 80%, more preferably 85% or more, still more preferably 90% or more, still more preferably 95% or more, most preferably 98% or more homology to the entire amino acid sequence.

For example, the peptide having sequence homology to the peptide represented by the amino acid sequence set forth in SEQ ID NO: 1 can be exemplified by a peptide represented by an amino acid sequence having, for example, 1 to 15, preferably 1 to 10, more preferably 1 to 5, still more preferably 1 to 3, still more preferably 1 or 2, most preferably 1 amino acid mutation such as deletion, substitution, addition, or insertion in the amino acid sequence set forth in SEQ ID NO: 1. The degree, position, and the like of an amino acid mutation are not particularly limited as long as the peptide having a mutation has substantially the same enucleation action as the peptide represented by the amino acid sequence set forth in SEQ ID NO: 1.

The peptide having a mutation may be naturally occurring one or one obtained by introducing a mutation based on a naturally occurring gene. Means for introducing a mutation is known per se, and, for example, site-directed mutagenesis, homologous gene recombination, primer extension, polymerase chain reaction (hereinafter, abbreviated as PCR), and the like can be used alone or in appropriate combination. For example, the introduction of a mutation may be performed in accordance with a method described in the literature (Sambrook et al. (ed.), "Molecular Cloning: A Laboratory Manual, Second Edition," 1989, Cold Spring Harbor Laboratory; Masami Muramatsu (ed.), "Laboratory Manual Gene Engineering," 1988, Maruzen Co., Ltd.), or by a modified method thereof, and Ulmer's technique (Ulmer, K. M., "Science," 1983, Vol. 219, p. 666-671) may also be employed. In the case of a peptide, for example, mutual substitutions between cognate amino acids (such as polar amino acids, non-polar amino acids, hydrophobic amino acids, hydrophilic amino acids, positively charged amino acids, negatively charged amino acids, and aromatic amino acids) are easily envisioned in terms of not changing basic natures (such as physical properties, functions, physiological activity, or immunological activity) of the peptide upon introducing a mutation.

The peptide can be produced by a gene engineering technique, chemical synthesis, and cell-free protein synthesis. The peptide after being produced can be further purified for the use thereof.

The peptide can be produced by a general gene engineering technique {Sambrook et al. (ed.), "Molecular Cloning: A Laboratory Manual, Second Edition," 1989, Cold Spring Harbor Laboratory; Masami Muramatsu (ed.), "Laboratory Manual Gene Engineering," 1988, Maruzen Co., Ltd.; Ulmer, K. M., "Science," 1983, Vol. 219, p. 666-671; Ehrlich, H. A. (ed.), "PCR Technology: Principles and Applications for DNA Amplification," 1989, Stockton Press} based on base sequence information of a gene encoding the peptide.

The peptide can also be produced by a general chemical synthesis method. For example, a solid phase synthesis method and a liquid phase synthesis method are known as the chemical synthesis method of the peptide, and any of them can be utilized. More specifically, such protein synthesis method encompasses a so-called step-wise elongation method in which each one amino acid is sequentially bound based on amino acid sequence information to elongate a chain, and a fragment condensation method in which a fragment formed of several amino acid residues is previously synthesized and then the respective fragments are subjected to a coupling reaction. A condensation method utilized in the above-mentioned protein synthesis method can also be carried out according to a standard method. The condensation method can be exemplified by an azide method, a mixed acid anhydride method, a DCC method, an active ester method, a redox method, a diphenylphosphoryl azide (DPPA) method, a DCC+additive (1-hydroxybenzotriazole, N-hydroxysuccinamide, N-hydroxy-5-norbornene-2,3-dicarboxylmide, and the like) method, and a Woodward method, and the like.

The peptide can be purified and/or separated by various separation methods utilizing, for example, its physical and chemical natures. For example, the separation methods can be exemplified by known methods such as ammonium sulfate precipitation, ultrafiltration, gel chromatography, ion exchange chromatography, affinity chromatography, high performance chromatography, and dialysis. Those methods can be used alone or inappropriate combination. Preferably, there is recommended a method including producing a specific antibody against the peptide based on the amino acid sequence information of the peptide and specifically adsorbing the peptide on the antibody, and for example, affinity chromatography utilizing a column to which the antibody is bound is recommended.

(Enucleation Inducer)

The "enucleation inducer" of the present invention includes one or more of the above-mentioned compounds derived from POMC. The enucleation inducer can also include the following carriers as needed in order to keep the enucleation induction action or stabilize the inducer.

Examples of the above-mentioned carrier include those usually used depending on the form in which a preparation is used, such as a filler, an extender, a binder, a moisturizing agent, a disintegrator, a lubricant, a diluent, and an excipient. More specific examples thereof include water, an organic solvent, collagen, polyvinyl alcohol, polyvinylpyrrolidone, a carboxyvinyl polymer, sodium alginate, water-soluble dextran, sodium carboxymethylstarch, pectin, xanthan gum, gum arabic, casein, gelatin, agar, glycerin, propylene glycol, polyethylene glycol, vaseline, a paraffin, stearyl alcohol, stearic acid, human serum albumin, mannitol, sorbitol, and lactose. Those are appropriately used alone or in combination of two or more kinds depending on a dosage form of the inducer of the present invention. Additionally, a stabilizer, a disinfectant, a buffer, a tonicity agent, a chelating agent, a surfactant, and a pH adjuster, and the like can also be used appropriately. For example, the stabilizer can be exemplified by human serum albumin, and an ordinary L-amino acid, a sugar, and a cellulose derivative. L-amino acid is not particularly limited, and may be any of, for example, glycine, cysteine, and glutamic acid. The sugar is also not particularly limited, and may be any of, for example, monosaccharides such as glucose, mannose, galactose, and fructose, sugar alcohols such as mannitol, inositol, and xylitol, disaccharides such as sucrose, maltose, and lactose, and polysaccharides such as dextran, hydroxypropyl starch, chondroitin sulfate, and hyaluronic acid, and derivatives thereof. The cellulose derivative is also not particularly limited, and may be any of methylcellulose, ethylcellulose, hydroxyethylcellulose, hydroxypropylcellulose, hydroxypropylmethylcellulose, carboxymethylcellulose sodium, and the like. The surfactant is also not particularly limited, and any of ionic surfactants and non-ionic surfactants can be used. The surfactant encompasses, for example, polyoxyethylene glycol sorbitan alkyl ester-based surfactants, polyoxyethylene alkyl ether-based surfactants, sorbitan monoacyl ester-based surfactants, and fatty acid glyceride-based surfactants. The buffer can be exemplified by boric acid, phosphoric acid, acetic acid, citric acid, ϵ-aminocaproic acid, glutamic acid, and/or corresponding salts thereof (e.g., alkali metal salts and alkaline earth metal salts thereof, such as sodium salts, potassium salts, calcium salts, and magnesium salts). The tonicity agent can be exemplified by sodium chloride, potassium chloride, sugars, and glycerin. For example, the chelating agent can be exemplified by sodium edetate and citric acid.

An amount of the compound derived from POMC, which is an active ingredient contained in the enucleation inducer according to the present invention, is appropriately selected from a wide range. The amount is suitably in the range of typically about 0.00001 to 70% by weight, preferably about 0.0001 to 5% by weight.

{Culture Medium (Medium)}

Any culture medium (medium) can be used as the "culture medium (medium)" of the present invention as long as ES cells, hematopoietic stem cells, erythroid precursor cells, nucleated erythrocytes, reticulocytes, or mature erythrocytes can be maintained and survive therein, or the culture medium by no means inhibits the maintenance, survival, differentiation, maturation, and self-replication of ES cells, hematopoietic stem cells, or erythroid precursor cells.

For example, the culture medium can also contain inorganic materials such as sodium, potassium, calcium, magnesium, phosphorus, and chlorine, and amino acids, vitamins, hormones, antibiotics, cytokines, fatty acids, sugars, or other chemical ingredients or biogenic substances such as serum depending on the purpose.

DMEM 10% FBS (including an antibiotic for cell culture) or the like can be used as one example.

(Culture Condition)

Any environmental condition may be employed for each of physical environmental conditions such as temperature, osmolality, and light, and chemical environmental conditions such as oxygen, carbon dioxide gas, pH, and redox potential for "culture conditions" of the present invention as long as ES cells, hematopoietic stem cells, erythroid precursor cells, nucleated erythrocytes, reticulocytes, or mature erythrocytes can be maintained and survive therein, or the condition by no means inhibits the maintenance, survival, differentiation, maturation, and self-replication of ES cells, hematopoietic stem cells, or erythroid precursor cells.

The temperature is 20 to 40° C., preferably about 37° C.

The osmolality is specifically an osmolality in a physiological condition, preferably an osmolality equivalent to that of saline.

A light condition may be a dark condition like a dark room, or may be a bright condition like an outside on a clear day.

An oxygen concentration may be specifically a dissolved oxygen concentration at which the culture system is in contact with a gas phase having an oxygen concentration of 10% or an oxygen concentration at which the culture system is in contact with a gas phase having an oxygen concentration of 30%, and is preferably an oxygen concentration at which the culture system is contacted with a gas phase having an oxygen concentration of 20%.

A general pH value in the culture system is 6.0 to 8.0, preferably a value equivalent to pH under the physiological condition. Carbon dioxide or any other buffer may be used for controlling the pH value.

A carbon dioxide concentration is specifically a dissolved carbon dioxide concentration at which the culture system is in contact with a gas phase having a carbon dioxide concentration of 5%.

The "method of enucleating a nucleated erythrocyte" of the present invention can utilize the following method, but is not particularly limited as long as the enucleation of an erythrocyte can be induced.

The cell density (including the nucleated erythrocytes) is adjusted to $1.0 \times 10^3$ to $1.0 \times 10^{10}$, preferably $1.0 \times 10^4$ to $1.0 \times 10^9$, more preferably $1.0 \times 10^5$ to $1.0 \times 10^7$, most preferably about $1.0 \times 10^6$ cells in 1 ml of the culture medium.

In addition, the compound derived from POMC is added to the culture medium so as to have a final concentration of 0.1 to 50 μM, preferably 0.5 to 30 μM, more preferably 0.7 to 20 μM, most preferably 1.0 to 10 μM. The compound may be added at a starting point of the culture, and may be additionally added during the culture in an appropriate manner.

A culture temperature is preferably 33 to 38° C., and a $CO_2$ concentration is preferably about 3 to 7%.

A culture period for inducing the enucleation of a nucleated erythrocyte derived from a fetal rat is 2 to 24 hours, preferably 3 to 12 hours, more preferably 4 to 8 hours.

The induction of an enucleated erythrocyte from the cultured hematopoietic stem cell derived from the human cord blood requires 20 days (see Non Patent Literature 4), but in the method of the present invention, the enucleation can be induced around on Day 15, and a half or more enucleation can be induced on Day 16.

It is conceivable that the difference in periods required for the enucleation in the human and the rat depends on the difference in periods required for the development of fetuses and survival days of erythrocytes.

The "method of culturing and/or proliferating an enucleated erythrocyte" of the present invention can utilize the following method, but is not particularly limited as long as the enucleation of a nucleated erythrocyte can be induced.

A hematopoietic stem cell or an erythroid precursor cell is differentiated into a nucleated erythrocyte by the method described above. Various cytokines are introduced into the culture medium as needed in the process of the differentiation. Subsequently, the compound derived from POMC is added to the culture medium so as to have a final concentration of 0.1 to 50 μM, preferably 0.5 to 30 μM, more preferably 0.7 to 20 μM, most preferably 1.0 to 10 μM during a time period in which the nucleated erythrocyte is present in the culture medium. The compound may be added at the starting point of the culture, and may be additionally added during the culture in an appropriate manner.

(Cytokine)

The "cytokine" of the present invention means a substance which is a proteinous factor which is released from cells and mediates an intercellular interaction, and exhibits a controlling action of an immune response, an anti-tumor action, an anti-viral action, a regulatory action on cell proliferation/differentiation, or the like. Specific examples thereof include interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interleukin-13 (IL-13), interleukin-14 (IL-14), interleukin-15 (IL-15), interleukin-16 (IL-16), interferon-α (IFN-α), interferon-β (IFN-β), interferon-γ (IFN-γ), granulocyte colony-stimulating factor (G-CSF), granulocyte-monocyte colony-stimulating factor (GM-CSF), a monocyte colony-stimulating factor, granulocyte-macrophage colony-stimulating factor, eosinophil granulocyte colony-stimulating factor, platelet colony-stimulating factor, stem cell factor (SCF), stem cell proliferation factor, flk2/flt3 ligand, leukemia inhibitory factor, erythropoietin (EPO), and macrophage-derived inflammatory protein-1α (MIP-1α). Preferred examples include interleukin-3, a stem cell factor (SCF), Flt-3L, granulocyte colony-stimulating factor, granulocyte-macrophage colony-stimulating factor, flk2/flt3 ligand, MIP-1α, and erythropoietin.

(Preservation Method for Enucleated Erythrocyte)

When the enucleated erythrocyte is preserved (including a long period of time), a method known per se can be used. The preservation method is, for example, a freezing preservation method. In this case, after a cryoprotectant such as Cell Banker (C) (Nippon Zenyaku Kogyo Co., Ltd.), glycerine, ethylene glycol, dimethyl sulfoxide (DMSO), sucrose, glucose, polyvinyl pyrrolidone (PVP), or trehalose is added as needed, the cell has only to be frozen slowly using a programmed freezer, and then stored in liquid nitrogen or the like.

(Agonist)

It is known that melanocortin receptors, MC2R and MC5R, which are target receptors of ACTH, are expressed on the surface of a nucleated erythrocyte.

In the present invention, the results of Example 6 below have confirmed that MC1R, MC2R, MC3R, MC4R, and/or MC5R, which are melanocortin receptors, are expressed on an erythroid precursor cell derived from a human.

Thus, the present invention includes an agonist which induces enucleation by acting on (binding to) MC1R, MC2R, MC3R, MC4R, and/or MC5R, which are melanocortin receptors on nucleated erythrocytes.

In addition, the present invention includes a method of enucleating a nucleated erythrocyte, including inducing enucleation by acting on (binding to) MC2R and/or MC5R, which are melanocortin receptors on nucleated erythrocytes.

The present invention is described in detail below with reference to specific examples, but the present invention is not limited thereto.

Example 1

Identification of Enucleation Rate of Nucleated Erythrocytes Derived from Fetal Rat by ACTH1-24

In this example, it was identified whether ACTH1-24 induced the enucleation of nucleated erythrocytes derived from a fetal rat or not. Details are as follows.

(Experimental Methods)

Experimental rats were bred, and peripheral blood was collected from 12 fetuses aged 13 days post coitum.

The collected peripheral blood was centrifuged at 1,000×g for 5 minutes at room temperature (centrifuge: Hitachi/05PR-22). Then, serum was removed, and blood cells were suspended in 10 ml of culture medium (supplemented with 10% FBS (Sigma/CR1211)/RPMI-1640 Medium (c) (Sigma/R8578)/1% penicillin-streptomycin (Sigma/P4333)) in a clean bench. This suspension was centrifuged again, a supernatant was removed, and the cells were resuspended in the culture medium. This manipulation was repeated twice, and finally the cells were suspended in 10 ml of the culture medium to prepare a sample for culturing peripheral blood.

A blood cell (cell) density was counted using about 10 μl of this sample and a hemocytometer (Burker-Turk Deep 1/10 mm/Erma Tokyo/7787), and the sample was diluted based on the counted value to adjust to $2\times10^6$ cells/ml.

This sample was diluted to a cell density of $1\times10^6$ cells/ml with the culture medium, to which ACTH1-24 (SEQ ID NO: 2, manufactured by Sigma) was added at a final concentration of 1 μM or 5 μM to use as a subject culture medium. The sample to which no ACTH1-24 was added was used as a control.

1 ml each of the various subject culture media was dispensed into a 4-well chamber slide glass (Chamber Slide™ System/Lab Tek (registered trademark)/177380), and cultured for a predetermined period of time in an incubator (Sakura $CO_2$ gas Incubator/Sakura/IC-160) under the condition at 37° C. at 5% $CO_2$.

At 0, 3, and 6 hours of the culture, the cells in each subject culture medium were fixed with glutaraldehyde (25% glutaraldehyde solution/Wako Pure Chemical Industries Ltd./073-00536) at a final concentration of 2%. DAPI (1 mg/ml of DAPI solution/DOJINDO/340-07971) for staining nuclei was dripped to the culture medium at a final volume ratio of 1/20,000, which was then shaken for 5 minutes, subsequently excited by a UV source using a fluorescence microscope (OLYMPUS IX70), and 10 fixed points were photographed. Then, the number of cells in the photograph was counted.

The enucleation rate was calculated as follows.

Enucleation rate (%)={Enucleated erythrocyte count/ Total cell count (Nucleated cell (including nucleated erythrocytes and mesenchymal stem cells) count+Enucleated erythrocyte count)}

(Results)

Figure 2:
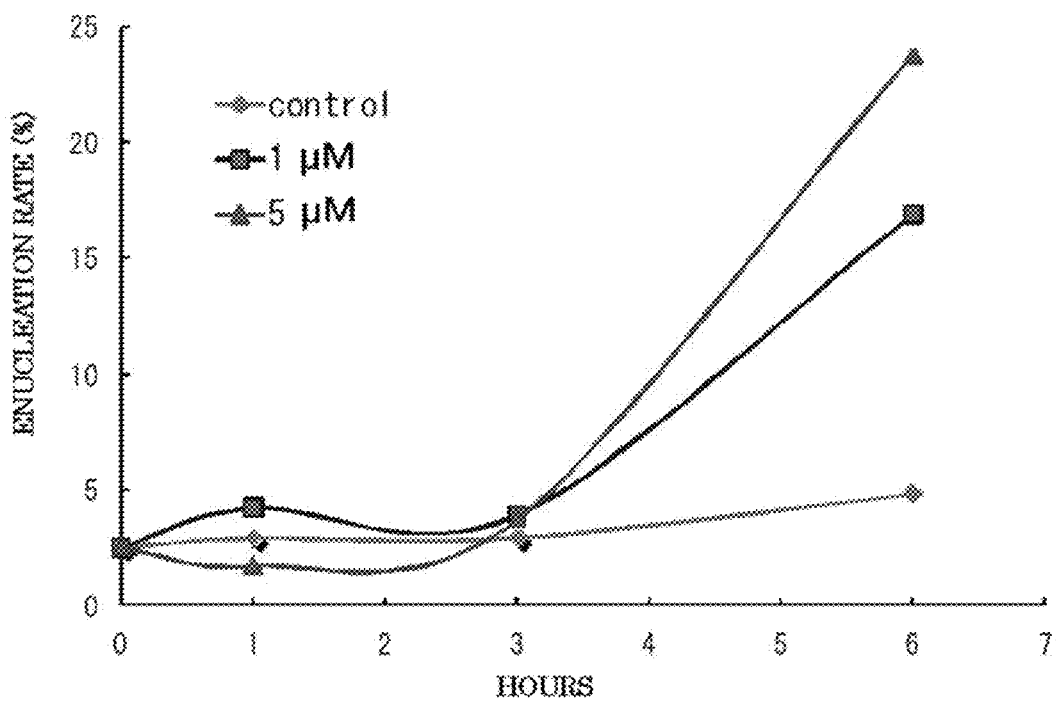
FIG. 2 shows an enucleation rate of nucleated erythrocytes derived from fetal rats in the case of using ACTH1-24.

The results of the above-mentioned experiment are shown in FIG. 2.

The enucleation was able to be induced after 6 hours in both fractions of ACTH1-24 added at 1 μM and 5 μM. That is, ACTH1-24 can induce the enucleation of an erythrocyte within a short time.

Example 2

Identification of Enucleation Rate of Nucleated Erythrocytes Derived from Fetal Rat by ACTH1-39

In this example, it was identified whether ACTH1-39 induced the enucleation of nucleated erythrocytes derived from a fetal rat or not. Details are as follows.

(Experimental Methods)

Two experimental rats (female) were bred, and peripheral blood was collected from 24 fetuses aged 13 days post coitum. The collected peripheral blood was centrifuged at 1,000×g for 5 minutes at room temperature. Then, serum was removed, and blood cells were suspended in 10 ml of culture medium (supplemented with 10% FBS (Sigma CR1211)/RPMI-1640 Medium (c) (Sigma R8578)/1% penicillin-streptomycin (Sigma/P4333)) in a clean bench. This suspension was centrifuged again, a supernatant was removed, and the cells were resuspended in the culture medium. This manipulation was repeated twice, and finally the cells were suspended in 10 ml of the culture medium to prepare a sample for culturing peripheral blood.

A blood cell (cell) density was counted using about 10 μL of this sample and a hemocytometer, and the sample was diluted based on the counted value to adjust to $2\times10^6$ cells/ml.

This sample was diluted to a cell density of $1\times10^6$ cells/ml with the culture medium, to which ACTH1-39 (SEQ ID NO: 1, manufactured by Sigma) was added at a final concentration of 5 μM to use as a subject culture medium. The sample to which no ACTH1-39 was added was used as a control.

250 μL each of the two kinds of the subject culture media were dispensed into a culture dish (MULTIWELL™ 48 well/FALCON/35-3078), and cultured in an incubator under the condition at 37° C. at 5% $CO_2$.

After culturing for 3 hours with or without the addition, a sample was collected, and fixed with glutaraldehyde at a final concentration of 2%. DAPI for staining nuclei was dripped onto this subject culture medium, which was then shaken for 5 minutes, and 80 μL of aliquot were collected, mounted on a silane-coating slide glass (Silane-coating slide glass/DAKO/S3003), and microscopically observed using a fluorescence microscope. A circumference centering on a droplet center was observed at a constant interval, and 9 fixed points were determined, and photographed. The number of cells on this photograph was counted, and the mean value of the counts from the nine photographs was calculated.

The enucleation rate was calculated in the same manner as in Example 1.

(Results)

Figure 3:
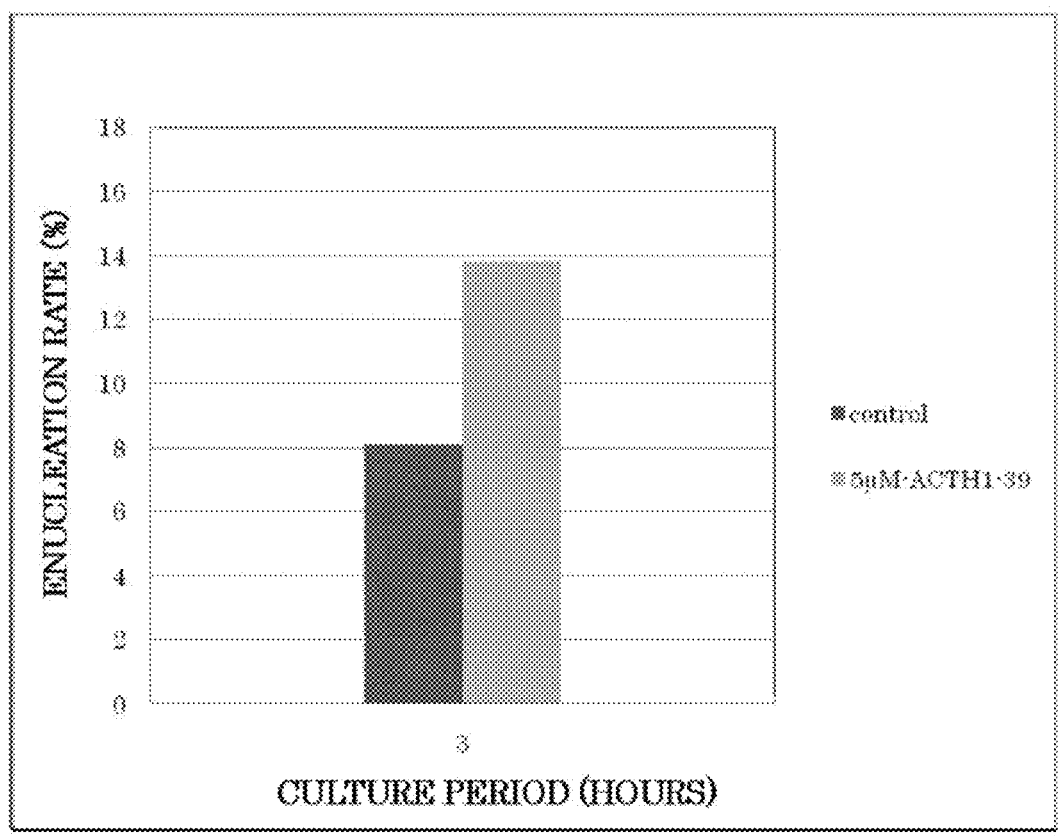
FIG. 3 shows an enucleation rate of nucleated erythrocytes derived from fetal rats in the case of using ACTH1-39.

The results of the above-mentioned experiment are shown in FIG. 3.

The enucleation rate in the fraction of ACTH1-39 added at 5 µM was higher than that in the control at 3 hours of the culture. That is, ACTH1-39 can induce the enucleation of a nucleated erythrocyte at 3 hours after its addition to the culture.

Figure 4:
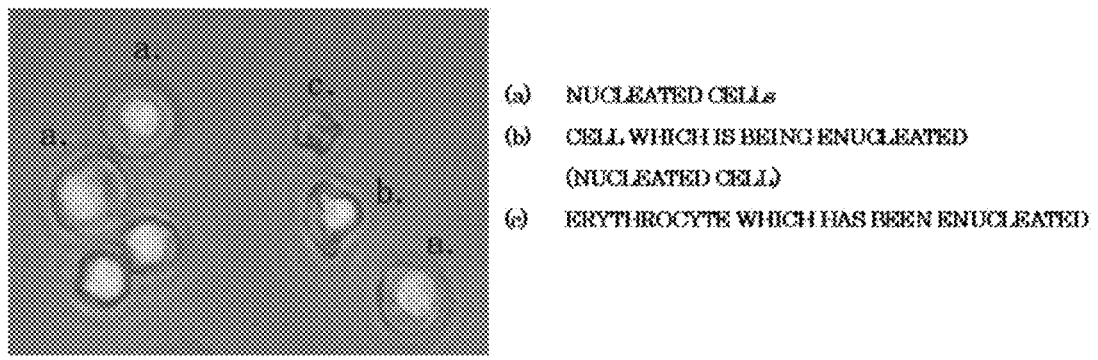
FIG. 4 shows an image of a sample cultured for 6 hours after adding ACTH1-39 to nucleated erythrocytes derived from fetal rats.

Further, a picture of the sample after culturing for 3 hours with the addition of 5 µM ACTH1-39 is shown in FIG. 4.

A nucleated cell ("a" in FIG. 4), a cell which was being enucleated ("b" in FIG. 4), and a erythrocyte which had been enucleated ("c" in FIG. 4) was able to be identified. This sample is derived from a phase in which nucleated erythrocytes and mesenchymal stem cells are mixed, and the nucleated cell ("a" in FIG. 4) is indistinguishable whether the cell is a nucleated erythrocyte or a mesenchymal stem cell by morphological observation under a microscope.

Example 3

Identification of Enucleation Rate of Nucleated Erythrocytes Derived from Fetal Rat by Clip or α-MSH In this example, it was identified whether each of CLIP and α-MSH induced the enucleation of nucleated erythrocytes derived from a fetal rat or not. Details are as follows.

(Experimental Methods)

Two experimental rats (female) were bred, and peripheral blood was collected from 24 fetuses aged 13 days post coitum. The collected peripheral blood was centrifuged at 1,000×g for 5 minutes at room temperature. Then, serum was removed, and blood cells were suspended in 10 ml of culture medium (supplemented with 10% FBS (Sigma CR1211)/ RPMI-1640 Medium (c) (Sigma R8578)/1% penicillin-streptomycin (Sigma P4333)) in a clean bench. This suspension was centrifuged again, a supernatant was removed, and the cells were resuspended in the culture medium. This manipulation was repeated twice, and finally the cells were suspended in 10 ml of the culture medium to prepare a sample for culturing peripheral blood.

A blood cell (cell) density was counted using about 10 µL, of this sample and a hemocytometer, and the sample was diluted based on the counted value to adjust to $2 \times 10^6$ cells/ml.

This sample was diluted to a cell density of $1 \times 10^6$ cells/ml with the culture medium, to which CLIP (SEQ ID NO: 11, manufactured by Sigma) or α-MSH (SEQ ID NO: 3, manufactured by Sigma) was added at a final concentration of 1 µM or 5 µM to use as a subject culture medium. The sample to which neither CLIP nor α-MSH was added was used as a control.

250 µl each of the various subject culture media were dispensed in an 8-well chamber slide glass (Chamber Slide™ System/Lab TekR/177402), and cultured for a predetermined period of time in an incubator under the condition at 37° C. at 5% $CO_2$. At 3, 6, and 9 (only for the 5-µM addition samples) hours of the culture, each subject culture medium was sampled, and the culture medium was fixed with glutaraldehyde at a final concentration of 2%. DAPI for staining nuclei was dripped to the culture medium, which was then shaken for 5 minutes, subsequently microscopically observed using a fluorescence microscope, and 10 field images were randomly determined and photographed. The number of cells in each of the photographs was counted, and the mean value thereof was calculated. The enucleation rate was calculated in the same way as in Example 1.

(Results)

Figure 5:
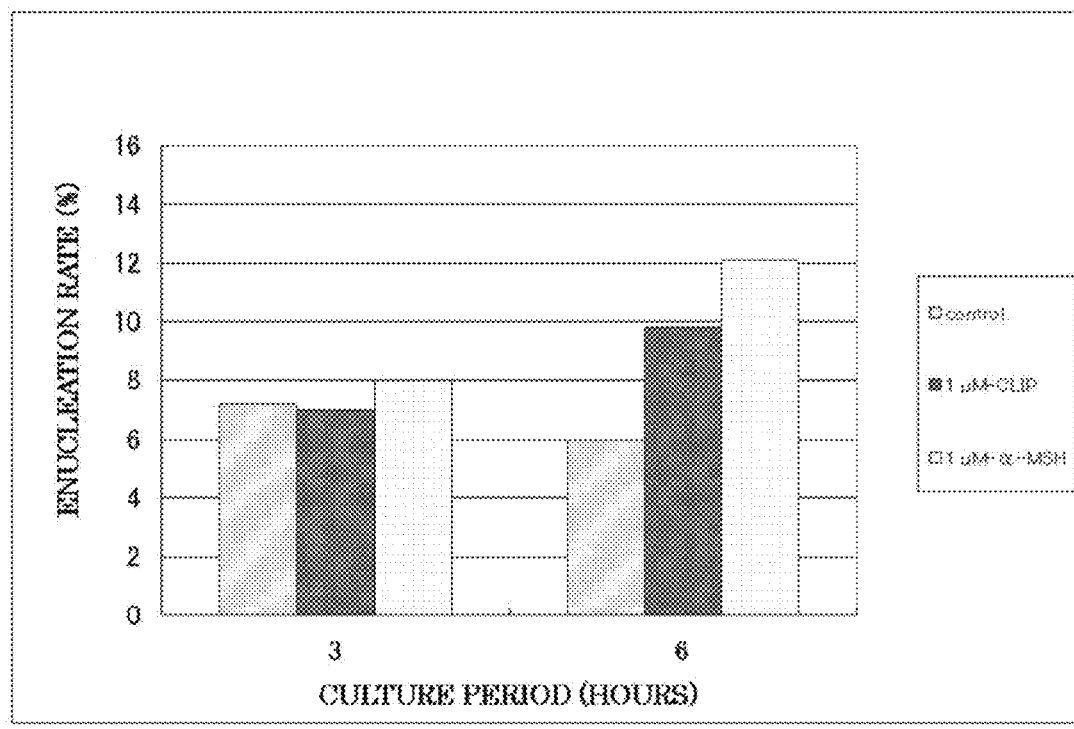
FIG. 5 shows enucleation rates of nucleated erythrocytes derived from fetal rats in the case of using CLIP and α-MSH (1 µM).

The results from the fractions of CLIP added at 1 µM and the fractions of α-MSH added at 1 µM are shown in FIG. 5. The enucleation was able to be induced after culturing for 6 hours with the addition of 1 µM of CLIP or α-MSH.

Figure 6:
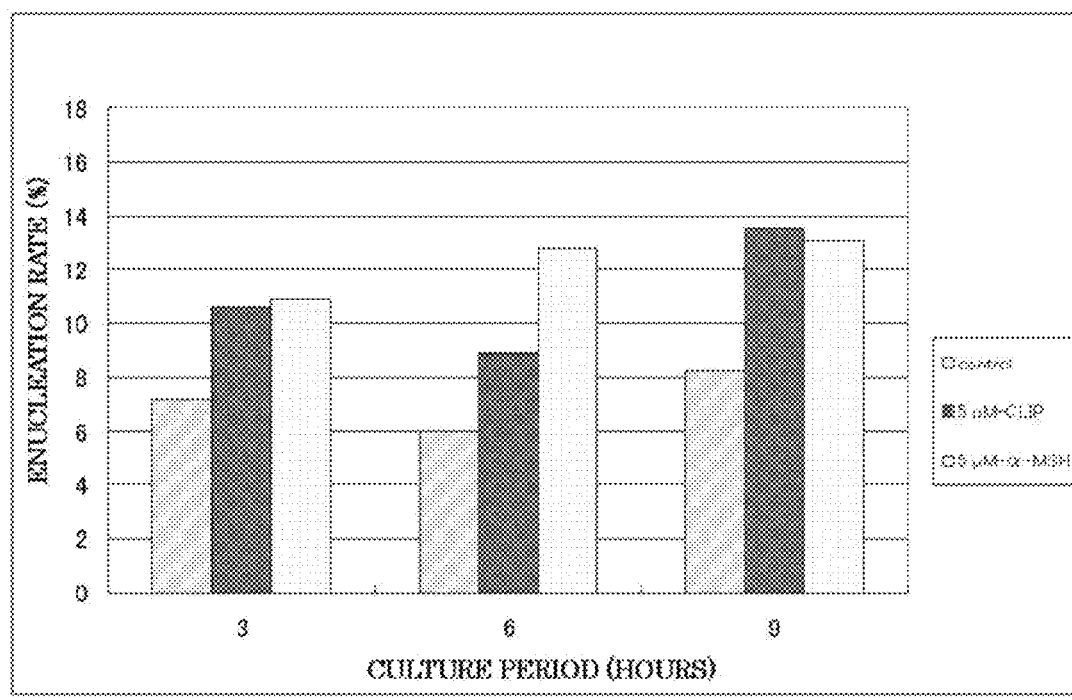
FIG. 6 shows enucleation rates of nucleated erythrocytes derived from fetal rats in the case of using CLIP and α-MSH (5 µM).

The results from the fractions of CLIP added at 5 µM and the fractions of α-MSH added at 5 µM are shown in FIG. 6. The enucleation was able to be induced after culturing for 3 hours with the addition of 5 µM of CLIP or α-MSH.

Example 4

Identification Of Enucleation Rate Of Nucleated Erythrocytes Derived from Fetal Human by ACTH1-24, ACTH1-39, CLIP, or α-MSH In this example, it was identified whether ACTH1-24, ACTH1-39, CLIP, or α-MSH induced the enucleation of erythrocytes derived from a human or not. Details are as follows.

(Culture Methods)

CD34-positive hematopoietic stem cells derived from a human (derived from the cord blood, 90% or more CD34-positive, product from Lonza: http://catalog.takara-bio.co.jp/product/basic_info.asp?unitid=U10 0004262) were cultured in HPGM medium. The cells at a density of $2 \times 10^4$ to $2 \times 10^5$ cells/ml were cultured with 25 ng/ml of SCF, 50 ng/ml of thrombopoietin, and 50 ng/ml of Flt-3 ligand for first 7 days, and this was used as a phase I.

Next, the cells at a density of $2 \times 10^5$ cells/ml were cultured with 3 U/ml of EPO, 25 ng/ml of SCF, 10 ng/ml of IL-3, and 10 ng/ml of IL-6, and this was used as a phase II. The cells were cultured with the addition of ACTH1-24, ACTH1-39, CLIP, or α-MSH at a concentration of 5.0 µM, or ACTH1-24 at a concentration of 0.5 µM on Day 4 in the phase II.

(Method of Measuring Enucleation Rate by DAPI Staining)

Figure 7:
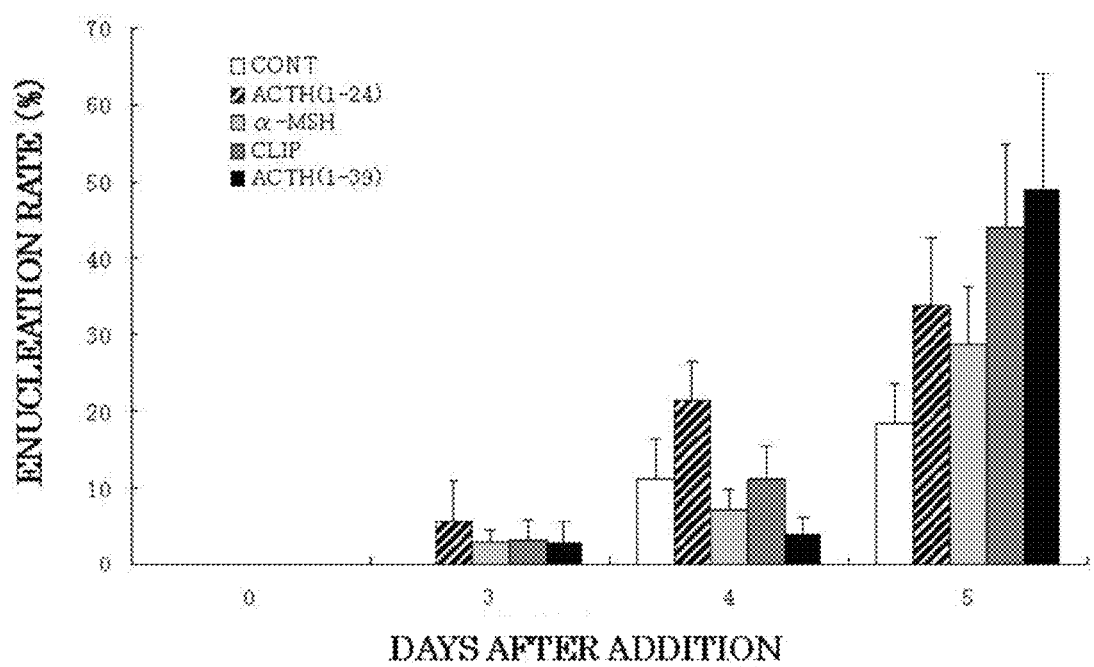
FIG. 7 shows enucleation rates of nucleated erythrocytes derived from human cord blood by ACTH1-24, CLIP, and α-MSH (5 µM).

The erythrocytes in the above-mentioned phase II cultured with ACTH1-24, ACTH1-39, CLIP, or α-MSH on Day 9 were fixed with 10% formalin, and stained with 4',6-diamidino-2-phenylindole (DAPI). Ten photographs were randomly taken under a fluorescence microscope, and the numbers of nucleated and enucleated erythrocytes were visually counted. The measurement was carried out in the blinded manner. The enucleation rate was calculated in the same manner as in Example 1. These results are shown in FIG. 7.

(Method of Measuring Enucleation Rate by Flow Cytometry)

Double staining for glycophorin A (Gly A) and the nucleus (propidium iodide, PI) was given to blood cells in the phase II cultured with ACTH1-24, CLIP, or α-MSH on Day 9 in the same manner as in the foregoing. The cells were analyzed using a flow cytometry (automatic cell analysis sorting apparatus, FACS Calibur/Becton Dickinson). Gly A-positive/PI-negative cells (corresponding to the left upper fraction of four dot plot fractions divided by data from flow cytometry in FIG. 9B) were determined as enucleated cells, and the enucleation rate of these enucleated cells relative to the total cells was calculated. These results are shown in FIG. 8.

(Results)

The results obtained by culturing cells with ACTH1-24, ACTH1-39, CLIP, or α-MSH at a concentration of 5.0 µM and calculating the enucleation rate by staining the cells with DAPI are shown in FIG. 7.

Figure 8:
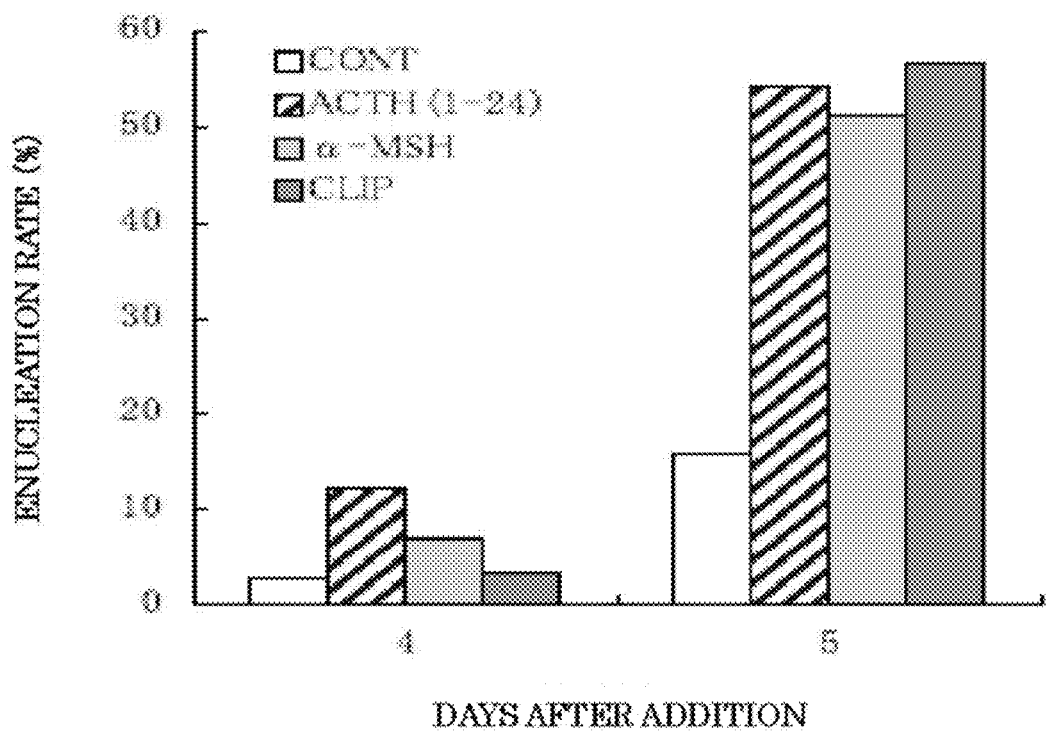
FIG. 8 shows enucleation rates of nucleated erythrocytes derived from human cord blood in the case of using ACTH1-24, ACTH1-39, CLIP, and α-MSH (0.5 µM).

Likewise, the results obtained by culturing cells with ACTH1-24, CLIP, or α-MSH at a concentration of 5.0 μM and calculating the enucleation rate by flow cytometry are shown in FIG. 8.

The results in FIG. 7 and FIG. 8 revealed that the enucleation of the nucleated erythrocytes was able to be induced by adding ACTH1-24, ACTH1-39, CLIP, or α-MSH to the nucleated erythrocytes derived from a fetal human.

Example 5

Identification of Enucleation Efficiency of Cells Derived from Human Cord Blood

In this example, the percentage of "enucleated erythrocytes" in "cells differentiating into erythrocytes" was identified. Details are as follows.

(Method of Identifying Enucleation Efficiency)

ACTH1-24 at a concentration of 0.5 μM was added to the culture carried out in the same manner as in Example 4, and the enucleation rate was measured by flow cytometry.

Gly A is a surface marker of erythroblasts, reticulocytes, and mature erythrocytes. Thus, this method was cited as a method of measuring the percentage of "enucleated erythrocytes"/"cells differentiating into erythrocytes" in a population of blood cells including immature erythrocytes (see Peng J. et al., Nat. Cell Biol., 10: 314-321, 2008).

(Results)

Figure 9:
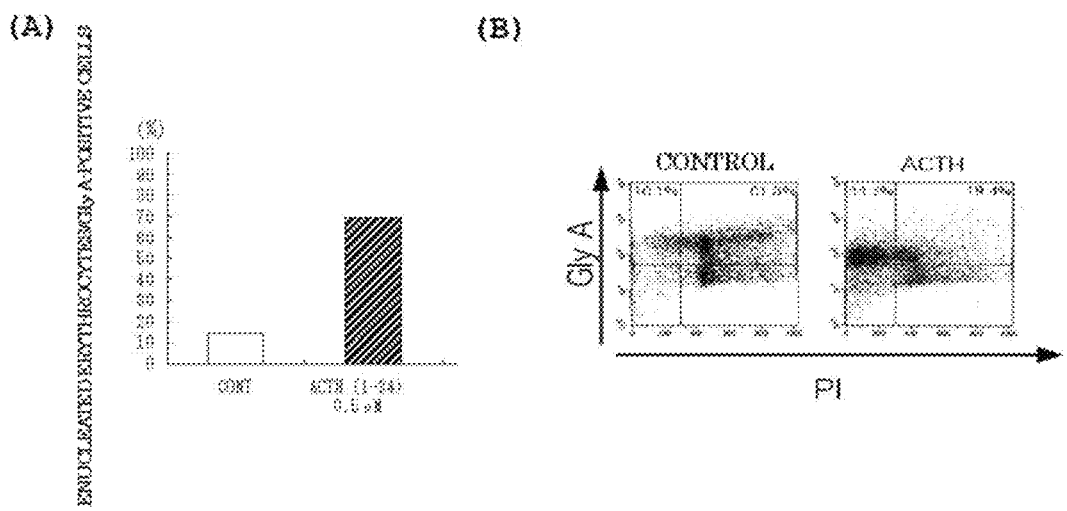
FIG. 9 shows enucleation induction efficiency of mature erythrocytes derived from human cord blood in the case of using ACTH1-24.

The results of the above-mentioned measurement are shown in FIG. 9. As is evident from the results in FIG. 9A, it was identified that about 70% of the cells differentiating into erythrocytes were enucleated.

Example 6

Identification of Melanocortin Receptor Expression on Erythrocytes

It is known that the melanocortin receptors (MC1R, MC2R, MC3R, MC4R, and MC5R) serve as receptors for ACTH and α-MSH. It is also known that ACTH reacts with MC1R to MC4R and α-MSH reacts with MC1R to MC5R (see Raffin-Sanson et al., J. Endocri., 149: 79-90, 2003, Entrez Gene in NCBI). In addition, it is known that MC5R is expressed on blood cells from a fetal mouse (see Nimura et al., Anat. Embryol., 211: 1096-117, 2006).

Thus, it was identified whether each melanocortin receptor was expressed on the erythroid precursor cells induced from the CD34-positive hematopoietic stem cells derived from the human cord blood in Example 4. More particularly, it was identified by RT-PCR that mRNA for the melanocortin receptors were expressed on the erythroid precursor cells. Details are as follows.

(Experimental Method)

The cells were cultured in the same manner as in Example 4, and the cells on Day 4 in the phase II were collected by centrifugation. Total RNA was extracted (RNAeasy, product from Qiagen), and RT-PCR was carried out using 1 μg of RNA (Takara Ex Taq Hot Start Version, product from Takara Bio).

Primers and the sizes of the resultant products are as follows.

```
MC2R:
forward:   ggcaaagacttgctttcctg   (SEQ ID NO: 20)

reverse:   cccacatgggaactaaatgg   (SEQ ID NO: 21)
           product size: 467

MC5R:
forward:   tggcagtggcggacatgctg   (SEQ ID NO: 22)

reverse:   ggcgatgatggcccctgagc   (SEQ ID NO: 23)
           product size: 260
```

(Results)

Figure 10:
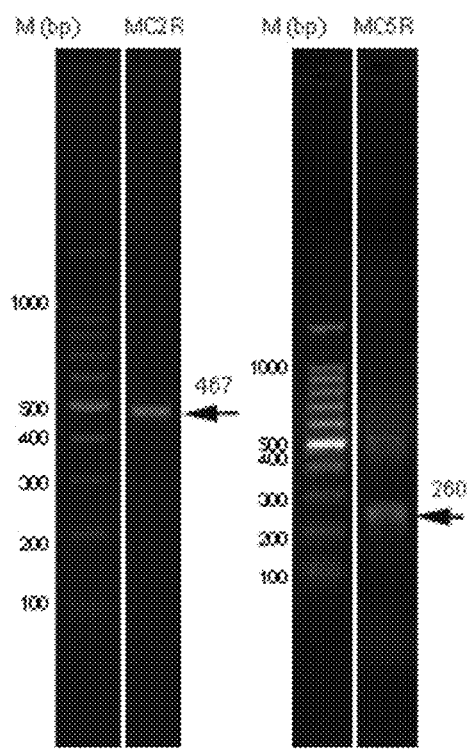
FIG. 10 shows confirmation of expression of MC2R and MC5R, which are melanocortin receptors, in erythroid precursor cells derived from human cord blood.

The results of the above-mentioned mRNA expression are shown in FIG. 10.

As is evident from the results in FIG. 10, it was identified that MC2R and/or MC5R, which were melanocortin receptors, were expressed on the erythroid precursor cells. Further, it was also identified that MC1R, MC3R, and MC4R were expressed on the erythroid precursor cells (not shown in the figure).

As described above, it is thought that the compound of the present invention derived from proopiomelanocortin (POMC) acts on (binds to) MC1R, MC2R, MC3R, MC4R, and/or MC5R, which are melanocortin receptors, on nucleated erythrocytes to induce the enucleation thereof.

That is, an agonist which acts on (binds to) MC1R, MC2R, MC3R, MC4R, and/or MC5R, which are melanocortin receptors on nucleated erythrocytes can be an active ingredient of an enucleation inducer.

(General Statements)

The results of Examples 1 to 5 in the foregoing revealed that ACTH1-39, ACTH1-24, CLIP, and α-MSH, which were compounds derived from POMC, were each able to induce enucleation within a short time.

Thus, the compound of the present invention derived from POMC was able to induce the enucleation in the final stage of the differentiation of erythrocytes derived from a mammal within a short time.

INDUSTRIAL APPLICABILITY

The present invention can provide the method of inducing the enucleation in the final stage of erythrocyte differentiation within a short time, and the enucleation inducer containing the compound.

This enables shortening of a period of producing blood and removal of a risk of canceration associated with transfusion of nucleated erythrocytes. That is, safe blood can be obtained within a short time and stably, and this greatly contributes to medical technologies.

The invention claimed is:

1. An enucleation inducer comprising a compound and a stabilizer, wherein the compound is selected from any one of the following peptides:
   (1) a peptide set forth in SEQ ID NO: 11;
   (2) a peptide set forth in SEQ ID NO: 13;
   (3) a peptide set forth in SEQ ID NO: 14;
   (4) a peptide set forth in SEQ ID NO: 15;
   (5) a peptide set forth in SEQ ID NO: 16;
   (6) a peptide set forth in SEQ ID NO: 18;
   (7) a peptide set forth in SEQ ID NO: 19;
   (8) a peptide having 98% or more homology to the peptide according to any one of the items (1) to (7) and having substantially the same enucleation induction action on a nucleated erythrocyte as the peptide;
   (9) a peptide having 1 to 2 amino acid substitutions, deletions, insertions, and/or additions in the peptide according to any one of the items (1) to (7) and having substantially the same enucleation induction action on a nucleated erythrocyte as the peptide,
   (10) a protected derivative, a glycosylated product, an acylated derivative, or an acetylated derivative of the peptide according to any one of the items (1) to (9); and
   (11) a peptide including the peptide according to any one of the items (1) to (9), and
      wherein the stabilizer is selected from human serum albumin, glucose, mannose, galactose, fructose, mannitol, inositol, xylitol, sucrose, maltose, lactose, dextran, hydroxypropyl starch, chondroitin sulfate, hyaluronic acid, methylcellulose, ethylcellulose, hydroxyethylcellulose, hydroxypropylcellulose, hydroxypropylmethylcellulose, and/or carboxymethylcellulose sodium.

2. A method of enucleating a nucleated erythrocyte, comprising culturing a separated nucleated erythrocyte in a culture medium containing the enucleation inducer of claim 1.

3. The method of claim 2 further comprising inducing enucleation in vitro through an action on MC1R, MC2R, MC3R, MC4R, and/or MC5R, which is a melanocortin receptor expressed on a nucleated erythrocyte.

* * * * *

SEQUENCE LISTING

```
<160> NUMBER OF SEQ ID NOS: 23

<210> SEQ ID NO 1
<211> LENGTH: 39
<212> TYPE: PRT
<213> ORGANISM: Unknown
```

```
<220> FEATURE:
<223> OTHER INFORMATION: ACTH

<400> SEQUENCE: 1

Ser Tyr Ser Met Glu His Phe Arg Trp Gly Lys Pro Val Gly Lys Lys
1               5                   10                  15

Arg Arg Pro Val Lys Val Tyr Pro Asn Val Ala Glu Asn Glu Ser Ala
            20                  25                  30

Glu Ala Phe Pro Leu Glu Phe
        35

<210> SEQ ID NO 2
<211> LENGTH: 24
<212> TYPE: PRT
<213> ORGANISM: Unknown
<220> FEATURE:
<223> OTHER INFORMATION: ACTH1-24

<400> SEQUENCE: 2

Ser Tyr Ser Met Glu His Phe Arg Trp Gly Lys Pro Val Gly Lys Lys
1               5                   10                  15

Arg Arg Pro Val Lys Val Tyr Pro
            20

<210> SEQ ID NO 3
<211> LENGTH: 13
<212> TYPE: PRT
<213> ORGANISM: Unknown
<220> FEATURE:
<221> NAME/KEY: ACETYLATION AND AMIDATION
<223> OTHER INFORMATION: alpha-MSH

<400> SEQUENCE: 3

Ser Tyr Ser Met Glu His Phe Arg Trp Gly Lys Pro Val
1               5                   10

<210> SEQ ID NO 4
<211> LENGTH: 22
<212> TYPE: PRT
<213> ORGANISM: Unknown
<220> FEATURE:
<223> OTHER INFORMATION: beta-MSH

<400> SEQUENCE: 4

Ala Glu Lys Lys Asp Glu Gly Pro Tyr Arg Met Glu His Phe Arg Trp
1               5                   10                  15

Gly Ser Pro Pro Lys Asp
            20

<210> SEQ ID NO 5
<211> LENGTH: 12
<212> TYPE: PRT
<213> ORGANISM: Unknown
<220> FEATURE:
<223> OTHER INFORMATION: gamma-,l,r,g

<400> SEQUENCE: 5

Tyr Val Met Gly His Phe Arg Trp Asp Arg Phe Gly
1               5                   10

<210> SEQ ID NO 6
<211> LENGTH: 17
<212> TYPE: PRT
<213> ORGANISM: Unknown
<220> FEATURE:
```

```
<223> OTHER INFORMATION: gamma-LPH

<400> SEQUENCE: 6

Tyr Gly Gly Phe Met Thr Ser Glu Lys Ser Gln Thr Pro Leu Val Thr
1               5                   10                  15
Leu

<210> SEQ ID NO 7
<211> LENGTH: 32
<212> TYPE: PRT
<213> ORGANISM: Unknown
<220> FEATURE:
<223> OTHER INFORMATION: beta-LPH

<400> SEQUENCE: 7

Tyr Gly Gly Phe Met Thr Ser Glu Lys Ser Gln Thr Pro Leu Val Thr
1               5                   10                  15

Tyr Gly Gly Phe Met Thr Ser Glu Lys Ser Gln Thr Pro Leu Val Thr
                20                  25                  30

<210> SEQ ID NO 8
<211> LENGTH: 32
<212> TYPE: PRT
<213> ORGANISM: Unknown
<220> FEATURE:
<223> OTHER INFORMATION: alpha-endorphin

<400> SEQUENCE: 8

Tyr Gly Gly Phe Met Thr Ser Glu Lys Ser Gln Thr Pro Leu Val Thr
1               5                   10                  15

Tyr Gly Gly Phe Met Thr Ser Glu Lys Ser Gln Thr Pro Leu Val Thr
                20                  25                  30

<210> SEQ ID NO 9
<211> LENGTH: 31
<212> TYPE: PRT
<213> ORGANISM: Unknown
<220> FEATURE:
<223> OTHER INFORMATION: beta-endorphin

<400> SEQUENCE: 9

Tyr Gly Gly Phe Met Thr Ser Glu Lys Ser Gln Thr Pro Leu Val Thr
1               5                   10                  15

Leu Phe Lys Asn Ala Ile Ile Lys Asn Ala Tyr Lys Lys Gly Glu
                20                  25                  30

<210> SEQ ID NO 10
<211> LENGTH: 17
<212> TYPE: PRT
<213> ORGANISM: Unknown
<220> FEATURE:
<223> OTHER INFORMATION: gamma-endorphin

<400> SEQUENCE: 10

Tyr Gly Gly Phe Met Thr Ser Glu Lys Ser Gln Thr Pro Leu Val Thr
1               5                   10                  15
Leu

<210> SEQ ID NO 11
<211> LENGTH: 22
<212> TYPE: PRT
<213> ORGANISM: Unknown
<220> FEATURE:
<223> OTHER INFORMATION: ,b,k,h,o
```

```
<400> SEQUENCE: 11

Arg Pro Val Lys Val Tyr Pro Asn Gly Ala Glu Asp Glu Ser Ala Glu
1               5                   10                  15

Ala Phe Pro Leu Glu Phe
            20

<210> SEQ ID NO 12
<211> LENGTH: 7
<212> TYPE: PRT
<213> ORGANISM: Unknown
<220> FEATURE:
<223> OTHER INFORMATION: peptide derived from POMC

<400> SEQUENCE: 12

Arg Pro Val Lys Val Tyr Pro
1               5

<210> SEQ ID NO 13
<211> LENGTH: 10
<212> TYPE: PRT
<213> ORGANISM: Unknown
<220> FEATURE:
<223> OTHER INFORMATION: ACTH1-10

<400> SEQUENCE: 13

Ser Tyr Ser Met Glu His Phe Arg Trp Gly
1               5                   10

<210> SEQ ID NO 14
<211> LENGTH: 14
<212> TYPE: PRT
<213> ORGANISM: Unknown
<220> FEATURE:
<223> OTHER INFORMATION: ACTH1-14

<400> SEQUENCE: 14

Ser Tyr Ser Met Glu His Phe Arg Trp Gly Lys Pro Val Gly
1               5                   10

<210> SEQ ID NO 15
<211> LENGTH: 16
<212> TYPE: PRT
<213> ORGANISM: Unknown
<220> FEATURE:
<223> OTHER INFORMATION: ACTH1-16

<400> SEQUENCE: 15

Ser Tyr Ser Met Glu His Phe Arg Trp Gly Lys Pro Val Gly Lys Lys
1               5                   10                  15

<210> SEQ ID NO 16
<211> LENGTH: 17
<212> TYPE: PRT
<213> ORGANISM: Unknown
<220> FEATURE:
<223> OTHER INFORMATION: ACTH1-17

<400> SEQUENCE: 16

Ser Tyr Ser Met Glu His Phe Arg Trp Gly Lys Pro Val Gly Lys Lys
1               5                   10                  15

Arg

<210> SEQ ID NO 17
<211> LENGTH: 7
```

```
<212> TYPE: PRT
<213> ORGANISM: Unknown
<220> FEATURE:
<223> OTHER INFORMATION: ACTH4-10

<400> SEQUENCE: 17

Met Glu His Phe Arg Trp Gly
1               5

<210> SEQ ID NO 18
<211> LENGTH: 32
<212> TYPE: PRT
<213> ORGANISM: Unknown
<220> FEATURE:
<223> OTHER INFORMATION: ACTH7-38

<400> SEQUENCE: 18

Phe Arg Trp Gly Lys Pro Val Gly Lys Lys Arg Arg Pro Val Lys Val
1               5                   10                  15

Tyr Pro Asn Val Ala Glu Asn Glu Ser Ala Glu Ala Phe Pro Leu Glu
            20                  25                  30

<210> SEQ ID NO 19
<211> LENGTH: 6
<212> TYPE: PRT
<213> ORGANISM: Unknown
<220> FEATURE:
<223> OTHER INFORMATION: ACTH4-9

<400> SEQUENCE: 19

Met Glu His Phe Arg Trp
1               5

<210> SEQ ID NO 20
<211> LENGTH: 20
<212> TYPE: DNA
<213> ORGANISM: artifical sequence
<220> FEATURE:
<223> OTHER INFORMATION: Forward primer for MC2R

<400> SEQUENCE: 20
ggcaaagact tgctttcctg                                              20

<210> SEQ ID NO 21
<211> LENGTH: 20
<212> TYPE: DNA
<213> ORGANISM: artifical sequence
<220> FEATURE:
<223> OTHER INFORMATION: Reverse primer for MC2R

<400> SEQUENCE: 21
cccacatggg aactaaatgg                                              20

<210> SEQ ID NO 22
<211> LENGTH: 20
<212> TYPE: DNA
<213> ORGANISM: artifical sequence
<220> FEATURE:
<223> OTHER INFORMATION: Forward primer for MC5R

<400> SEQUENCE: 22
tggcagtggc ggacatgctg                                              20

<210> SEQ ID NO 23
<211> LENGTH: 20
<212> TYPE: DNA
```

```
<213> ORGANISM: artifical sequence
<220> FEATURE:
<223> OTHER INFORMATION: Reverse primer for MC5R

<400> SEQUENCE: 23
ggcgatgatg gcccctgagc                                              20
```